US008650041B2

(12) United States Patent
Thorsell et al.

(10) Patent No.: US 8,650,041 B2
(45) Date of Patent: Feb. 11, 2014

(54) METHOD AND DEVICE FOR PROVIDING COMPENSATED STAFF DATA

(76) Inventors: Kajsa Thorsell, Hässleholm (SE); Berit Nordström, Ängelholm (SE); Bengt Sivberg, Lund (SE)

( * ) Notice: Subject to any disclaimer, the term of this patent is extended or adjusted under 35 U.S.C. 154(b) by 48 days.

(21) Appl. No.: 13/061,172

(22) PCT Filed: Aug. 28, 2009

(86) PCT No.: PCT/SE2009/000395
§ 371 (c)(1),
(2), (4) Date: Jun. 6, 2011

(87) PCT Pub. No.: WO2010/024748
PCT Pub. Date: Mar. 4, 2010

(65) Prior Publication Data
US 2011/0238436 A1 Sep. 29, 2011

Related U.S. Application Data

(60) Provisional application No. 61/136,355, filed on Aug. 29, 2008.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC .............................................................. 705/2
See application file for complete search history.

(56) References Cited

U.S. PATENT DOCUMENTS

| 2004/0249676 A1 | 12/2004 | Marshall et al. |
| 2006/0111939 A1* | 5/2006 | Bixler et al. ..................... 705/2 |
| 2006/0277074 A1* | 12/2006 | Einav et al. ...................... 705/3 |
| 2009/0089092 A1 | 4/2009 | Johnson et al. |

FOREIGN PATENT DOCUMENTS

| EP | 0 652 528 A2 | 5/1995 |
| WO | 00/55751 A1 | 9/2000 |

OTHER PUBLICATIONS

Nijman, Fifteen years of research with the Staff Observation Aggression Scale: a review, 2005, Acta Psychiatrica Scandinavica, vol. 111, Issue 1, pp. 12-21.*
EPO: "Mitteilung des Europäischen Patentamts vom 1. Oktober 2007 über Geschäftsmethoden = Notice from the European Patent Office dated Oct. 1, 2007 concerning business methods" Official Journal of the European Patent Office. vol. 30, No. 11, Nov. 1, 2007, pp. 592-593, XP002498048, ISSN: 0170-9291.

(Continued)

*Primary Examiner* — Tran Nguyen
(74) *Attorney, Agent, or Firm* — Ladas & Parry LLP

(57) ABSTRACT

The present invention relates to a method, device and a computer program product for compensated staff data for one or more care units which are related to a plurality of care unit observations. The method comprises receiving staff data, receiving patient data relating to a plurality of care need parameters, determining a care need for each of a plurality of patients based on the patient data, receiving care unit data, and generating compensated staff data for the one or more care units based on the care need, the staff data and the care unit data, and transmitting the compensated staff data. By using the invention, compensated staff data may be provided in an efficient and reliable manner.

9 Claims, 7 Drawing Sheets

(56) References Cited

OTHER PUBLICATIONS

Statement in Accordance with the Notice From the European Patent Office Dated Oct. 1, 2007 Concerning Business Methods—EPC, Nov. 1, 2007, XP002456252.

Supplemental European Search Report; dated Oct. 8, 2012, EP09810298.

International Search Report: mailed Nov. 25, 2009; PCT/SE2009/000395.

* cited by examiner

METHOD AND DEVICE FOR PROVIDING COMPENSATED STAFF DATA

FIELD OF THE INVENTION

The present invention relates to the field of controlling staff resources in health care. In particular, it relates to a method and device for providing compensated staff data for one or more care units.

BACKGROUND OF THE INVENTION

The need for health care is growing in our society for a number of reasons. For example, the population is becoming older and the methods for treating diseases are becoming more advanced. Further, diseases which are related to the modern way of living are increasing at a high rate. Examples of such diseases are stress, fatness and drug addiction. As a consequence, the costs for care are growing and accordingly the available resources, in terms of money and competence, should be used in an efficient manner.

Traditionally, and still today, resources are planned in relation to the number of persons receiving care or the number of beds in a care unit. Thus, two care units having equally many beds will also have equally many staff members. Since the staff resources per patient in this way become equal, this may have as a result that severely ill patients receive too little care in comparison to patients having only a mild care need. Thus there is a need for improvements for controlling staff resources in health care.

SUMMARY OF THE INVENTION

It is an object of the present invention to overcome this problem, and to provide a method, a device and a computer program product which provide an improved control of staff resources in one or more care units.

According to a first aspect of the invention the above object is achieved by a method for providing compensated staff data for one or more care units, the one or more care units being related to a plurality of care unit observations, the method comprising receiving staff data comprising the number of staff members associated with each care unit observation, receiving patient data associated with a plurality of patients, wherein each of the plurality of patients is associated with one of the plurality of care unit observations, the patient data relating to a plurality of care need parameters, determining, by a processing unit, a care need for each of the plurality of patients based on the patient data, receiving care unit data comprising the number of beds associated with each of the plurality of care unit observations, generating, by the processing unit, compensated staff data for the one or more care units based on the care need, the staff data and the care unit data, and transmitting the compensated staff data.

The present invention is based on the realization that by taking the care need for the patients into account, the staff resources for the one or more care units may be controlled in an efficient manner. For example, according to the present invention, a care unit having patients with a large care need may be assigned a larger number of staff members per patient than a care unit where the patients have less need of care. Thus, the number of staff members is compensated with respect to care need. Further, by using data associated with several care unit observations, such as data from a large number of care units or data collected over period in time, the provided compensated staff data becomes reliable, since information collected from several data sources is combined when generating the compensated staff data.

In general it is difficult to estimate a patient's need of care since there are many aspects of the care need that have to be taken into account. However, by letting the care need depend on a plurality of care need parameters, the problem of estimating the care need may be simplified in that a limited number of care need parameters may be used to represent a patient's care need. For example, the care need parameters may represent the most important aspects of the care need, such as the most time consuming care activities. In this way, the amount of data which is needed to determine a patient's care need is reduced, thereby in turn reducing the need of memory capacity. Further, as the amount of data to represent the care need is reduced, the demand for processing capacity is reduced since fewer operations are required to determine the care need.

Throughout the disclosure the term "care unit" is used as a general term for an organized unit handling the care of a plurality of patients. The type of care is to be interpreted widely. Examples of a care unit are a unit in a home for old people, a unit carrying out domestic help, a care unit for drug addicts etc.

Further, the term "care unit observation" is to be interpreted as an observation of data relating to a particular care unit at a particular point in time. Examples of such observed data are patient data relating to the care need of a plurality of patients in the care unit, staff data relating to the number of staff members in the care unit and care unit data relating to the number of beds in the care unit.

Still further, the term "care need parameter" is to be generally interpreted as a parameter which may influence the care need of a patient. For example, a patient may need help with washing, dressing, medication, nutrition etc. Other examples of parameters influencing the care need may be the patient's cognitive ability, such as the level of the patient's verbal communication ability or the patient's temper or sense of locality.

In general, the plurality of care unit observations are related to one or more care units. For example, the plurality of care unit observations may be related to a single care unit which is observed at several points in time, thereby giving rise to a plurality of care unit observations. Alternatively, the plurality of care unit observations may be related to several care units which are observed at the same or at different occasions.

Optionally, at least two of the plurality of care unit observations are associated with different points in time. In this way a care need in the care units changing over time may be taken into account. For example, the care need of a particular patient may increase or decrease, or patients may leave the care unit and be replaced by other patients having a different care need may be taken into account. By allowing at least two of the care units to be associated with different points in time, knowledge from data relating to previous care unit observations may be combined with data from newer care unit observations in order to generate compensated staff data for the care units being associated with the newer care unit observations. An advantage is thus that the method may provide compensated staff data which is updated as the care need in a care unit changes.

Optionally, one of the different points in time is present time. In this way, previous and present care unit observations may be combined in order to provide compensated staff data which is current for the one or more care unit.

Further, the compensated staff data may be generated for a plurality of care units, wherein each of the plurality of care units is related to one care unit observation. This may be advantageous if there are many care units, for example associated with a common local authority such as a municipality, which should share the same resources. In such a situation simultaneous observations of the care units may be used. In this way, data from all care units may be combined in order to simultaneously generate compensated staff data for the plurality of care units.

Optionally, the patient data associates each patient with a plurality of care need points, wherein each of the plurality of care need points corresponds to one of the plurality of care need parameters, and wherein the step of determining a care need for each of the plurality of patients comprises adding, for each patient, the plurality of care need points. This is advantageous since it is computationally efficient to represent the care need parameters in terms of points which easily may be manipulated numerically, for example by computing a sum.

Further, the care need points may be represented by a number. In particular the plurality of care need points may take values in a discrete set of ordered numbers. In this way, the care need points may easily be assigned values that indicate the amount of care a certain patient needs. Moreover, a computer may efficiently represent and store numbers and thereby the need for memory capacity may be reduced by representing the care need in terms of a number.

Further, the plurality of care need points may be associated with at time duration. This is advantageous when determining a care need for each patient by for example adding the care need points, since care need points associated with different care need parameters have a similar interpretation. Moreover, with this arrangement, the care need may be interpreted in terms of the time spent by the staff on each patient. For instance, if a patient has a care need point of 2 for a certain care need parameter and if the plurality of care need points is associated with a time duration of 5 minutes, the time duration for the care activity associated with the particular care need parameter is equal to 10 minutes.

Optionally, the method may further comprise receiving care time data which associates each of the plurality of care need points with the time duration. This may be advantageous in that the time duration associated with the care need points easily may be adjusted based on measurements made by the staff in the care units. Thereby a flexible way to provide compensated staff data may be achieved.

In general, the generating of compensated staff data may be performed in many fashions as long as the care need, the staff data and the care unit data are combined into compensated staff data. Optionally, the generating of compensated staff data may comprise determining, for each care unit observation, an average care need based on the care need for each of the plurality of patients, and determining, for each care unit observation, a weighted average care need by weighting the average care need by using the staff data and the care unit data. With this arrangement, by determining an average care need the average workload per patient may be estimated. Further, by weighting the average care need by using the staff data and the care unit data, it may be determined how this workload may be shared by the staff members.

Optionally, the method may comprise determining, for each care unit observation, a weight, wherein the weight is determined by dividing the number of staff members for the care unit observation by the number of beds for the care unit observation, and wherein the weighted average care need is determined by dividing, for each care unit observation, the average care need by the weight. In this way, the amount of care need to be handled by each staff member may be determined. More precisely, by dividing the average care need by the weight, the average care need may be multiplied by the number of beds, thereby generating the total care need for the care unit which in turn is divided by the number of staff members.

The step of generating compensated staff data may further comprise determining a total weighted average by averaging the weighted average care need for the plurality of care unit observations. This is advantageous since data from several care unit observations may be combined and thereby an overview of the care need and the workload among the staff members may be obtained. This overview may be advantageous in that it for example provides useful information of how the staff resources may be redistributed. Moreover, in case the weighted average care need for the care unit observations is interpreted as the care need handled by each staff member, the total weighted average is interpreted as being the average care need handled by each staff member.

The method may further comprise determining compensated staff data for the one or more care units by multiplying, for each care unit observation, the average care need by the number of beds for the care unit observation and by dividing it by the total weighted average. With this arrangement, the compensated staff data may be generated by taking data from all care unit observations into account. In particular, in case the total weighted average is interpreted as the care need handled by each staff member, the compensated staff data may be determined as the total care need for a care unit observation divided by the care need which each staff member may handle. Thus, in this way data from the plurality of care unit observations are used to obtain an estimate of the workload which each staff member may handle, which in turn may be used to determine compensated staff data.

Optionally, the staff data may comprise information relating to a competence of the number of staff members, wherein the competence of the number of staff members is used in the step of generating compensated staff data. For example, a competence may refer to the experience of the staff member or the level of skills of the staff member. A nurse, an assistant nurse or an assistant are examples of different levels of skills of a staff member. Moreover, the competence of the staff members may be taken into account when generating compensated staff data by, for example, performing the method separately for different staff competences or by relating the different care need parameters to different kinds of staff competences. For instance, some care actions, such as giving medication, may only be performed by nurses whereas other care actions, such as washing the patient, may be handled by assistants.

Optionally, the plurality of care need parameters are grouped into three groups relating to general care, medical care and cognitive care, wherein the group relating to general care comprises the care need parameters nutrition, washing upper body, washing lower body, toilet visits, dressing/undressing, mobilization, observation/supervision/alarm and social activities, the group relating to medical care comprises the care need parameters wound treatment, catheter/stoma, administration, injection, rehabilitation, and the group relating to cognitive care comprises the care need parameters orientations/sense of locality, verbal communication, confusion, anxiety, and temper. By using such groups of care need parameters, not only medical care is taken into account when determining the care need for a patient, but also other kinds of care which are important for the patient's well being may be taken into account. Further, the inventors have performed extensive studies in order to validate that the above care need parameters can be used in order to obtain a reliable measure of the care need. More precisely, the inventors have found that the above disclosed care need parameters are many enough to measure the major part of the care need, while the number of care need parameters still is kept as low as possible. In this way the memory capacity and computational efforts may be kept at a minimum at the same time as a reliable result is provided.

According to a second aspect of the invention the above object is achieved by a device for providing compensated staff data for one or more care units, said one or more care units being related to a plurality of care unit observations, the device comprising a receiver arranged to receive staff data comprising the number of staff members associated with each care unit observation, to receive patient data associated with a plurality of patients, wherein each of the plurality of patients is associated with one of the plurality of care unit observations, the patient data relating to a plurality of care need parameters, and to receive care unit data comprising the number of beds associated with each of the plurality of care unit observations, a processing unit arranged to determine a care need for each of the plurality of patients based on the patient data, and to generate compensated staff data for the one or more care units based on the care need, the staff data and the care unit data, and a transmitter arranged to transmit said compensated staff data.

The receiver of the device may further be arranged to receive care time data from one or more time measuring units.

According to a third aspect of the invention the above object is achieved by a computer program product stored on a computer-readable medium comprising computer program code portions adapted to perform the method according the first aspect of the invention when loaded and executed on a computer.

Features and advantages of first aspect generally apply to the second and third aspects.

It is noted that the invention relates to all possible combinations of features recited in the claims.

Generally, all terms used in the claims are to be interpreted according to their ordinary meaning in the technical field, unless explicitly defined otherwise herein. All references to "a/an/the [device, event, message, alarm, parameter, step etc.]" are to be interpreted openly as referring to at least one instance of said device, event, message, alarm, parameter, step etc., unless explicitly stated otherwise. The steps of any method disclosed herein do not have to be performed in the exact order disclosed, unless explicitly stated.

BRIEF DESCRIPTION OF THE DRAWINGS

Embodiments of the present invention will be described, by way of example, with reference to the accompanying schematic drawings, in which.

DETAILED DESCRIPTION

In the accompanying drawings certain embodiments are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Devices will be described in an operating mode. Like numbers refer to like elements throughout.

Figure 1:
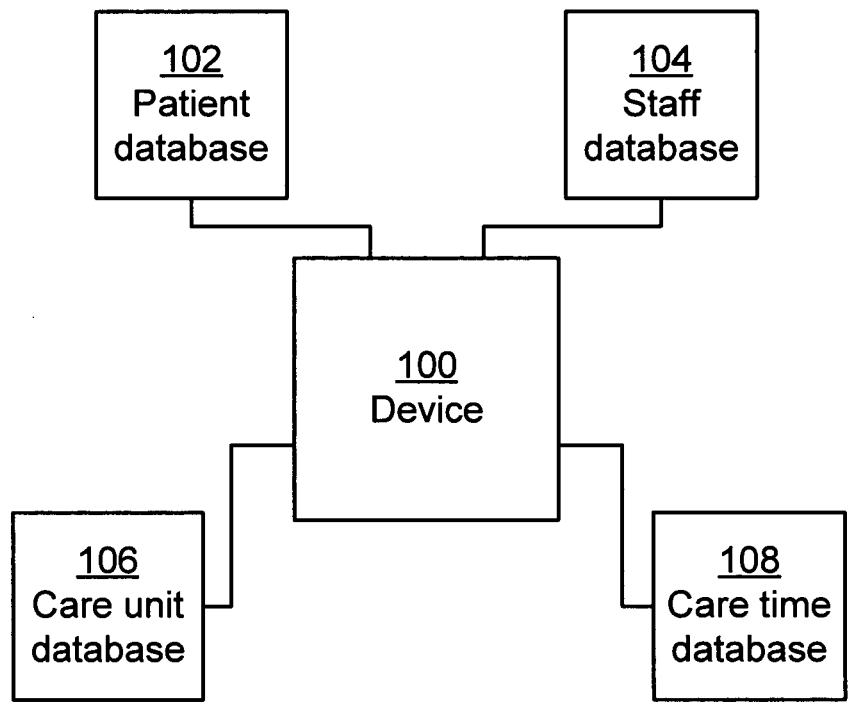
FIG. 1 is a schematic view of a device according to embodiments.

FIG. 1 is a schematic view of a device 100 according to embodiments of the invention. The device 100 may be (part of) a computer, laptop computer, and the like. The device 100 is configured to be wired or wirelessly operatively connected to inter alia a patient database 102, a staff database 104, a care unit database 106, and a care time database 108.

The patient database 102 comprises patient data associated with a plurality of patients. In particular, it may comprise patient data relating to a plurality of care need parameters for each of the plurality of patients. It may further comprise care need points corresponding to the care need parameters for each of the plurality of patients. The staff database 104 comprises data relating to the number of staff members associated with each of a plurality of care unit observations. Moreover, the staff database 104 may comprise information relating to the competence of the staff members. For example, it may comprise the experience of the staff members and/or the level of skills of the staff members. The care unit database 106 comprises data relating to a plurality of observations of one or more care units. In particular, it may comprise the number of beds associated with the plurality of care unit observations. The care time database 108 may comprise care time data associating each care need point with a time duration. The care time database 108 may further be connected to one or more time measuring units (not shown) by which the time duration for the care of the plurality of patients may be measured. The time measuring unit may comprise a bar code reader which is arranged to start a clock when a first bar code is read and to stop a clock when a second bar code is read. Further, the first and second bar codes may be associated with the individual patients. In this way the time duration for the care of the plurality of patients may be efficiently measured. Some of the databases 102, 104, 106, and 108 may be comprised in the device 100.

Figure 2:
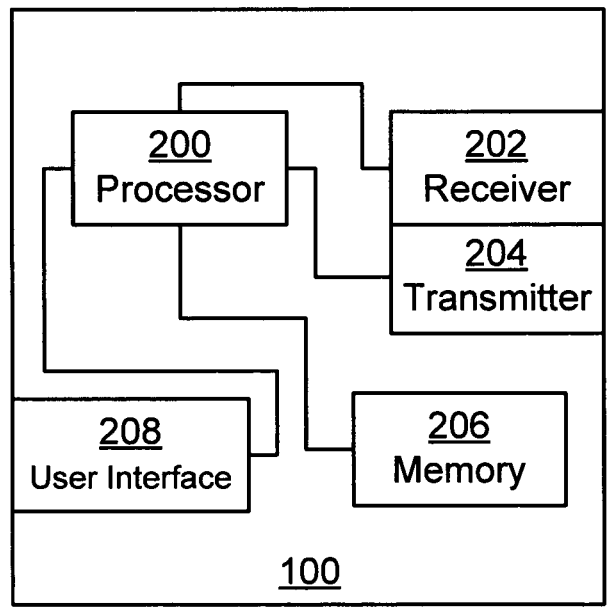
FIG. 2 is a schematic view of internal components of a device according to embodiments.

FIG. 2 is a schematic view of internal components of the device 100 of FIG. 1 according to embodiments of the invention. The device 100 comprises a processing unit 200, or processor, which may be a central processing unit (CPU). The processing unit 200 is arranged to be operatively connected to a receiver 202, a transmitter 204, and a memory 206. The receiver 202 is configured to receive data signals from external units, devices, and apparatuses in any known manner. For example, the receiver 202 may be configured to receive data from the patient database 102, the staff database 104, the care unit database 106, and the care time database 108. Likewise, the transmitter 204 is configured to transmit data signals to external units, such as a display, devices, and apparatuses in any known manner. The receiver 202 and the transmitter 204 may be part of a common transceiver configured to both receive and transmit data. The memory 206 may be configured to store software instructions pertaining to a computer-implemented method for providing compensated staff data. The memory 206 may thus form a computer-readable medium which may have stored thereon software instructions. The software instructions may cause the processing unit 200 to execute a method according to embodiments of the present invention.

The device 100 may further comprise a user interface 208 which is arranged to receive user instructions and to present data processed by the processing unit 200 and/or received by the receiver 202 to a user. The user instructions may for example pertain to selecting care units, time points, care need parameters, and/or staff competences.

Figure 3:
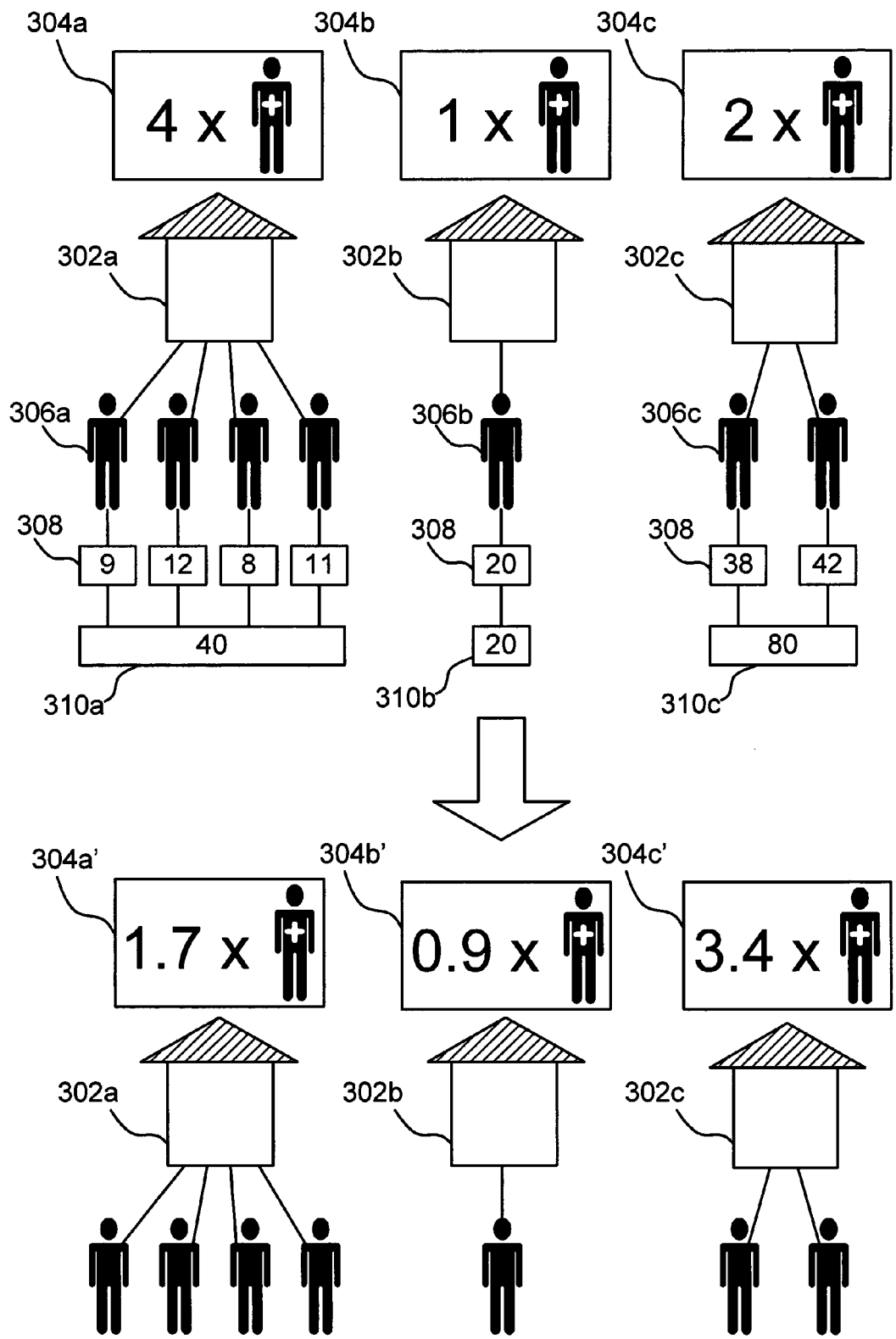
FIG. 3 is a schematic illustration of care unit observations and compensated staff data according to embodiments.

FIG. 3 is a schematic illustration of care unit observations. The upper part of FIG. 3 illustrates three care unit observations. The care unit observations are related to care units 302a, 302b, and 302c. Care units 302a-c may be three different care units or the same care unit observed at different time points. Alternatively, the care units 302a-c may correspond to two different care units one of which is observed twice at different time points. For example, care units 302a-b may correspond to a first care unit observed at a first and a second time point, and care unit 302c may correspond to a second care unit observed at the first time point, the second time point or at a third time point. The care unit observations are further associated with staff data 304a-c comprising the number of staff members. The device 100 may receive the staff data 304a-c by the receiver 202 via a wired or wireless connection from the staff database 104. The staff database 104 may for example be part of a remote server transmitting the staff data 304a-c to the device 100 via a communications network (not shown). The staff data 304a-c may be inputted in the staff database 104 by an operator. Alternatively, the staff data 304a-c may be received by the device 100 as a user input, for example via the user interface 208. In this case, the staff data may be stored in the memory 206 of the device 100. In this example, care unit 302a is associated with four staff members, care unit 302b is associated with one staff member, and care unit 302c is associated with two staff members. Further, each care unit observation is associated with at least one patient 306a-c. Here, care unit 302a is associated with four patients 306a, care unit 302b, with one patient 306b and care unit 302c with two patients 306c. Data regarding patients may be inputted in the device 100 by a staff member. For example, the device 100 may receive data regarding the patients via the user interface 208. Alternatively, patient data may be received by the patient database 102 which in turn may communicate the data to the device 100 via a wired or wireless connection. In this example, the number of staff members is determined in the traditional fashion, that is, the number of staff members is proportional to the number of patients or to the number of beds in the care unit. In this example, the number of beds is assumed to be equal to the number of patients. Each patient 306 is in turn associated with a care need 308. Data relating to the care need of the patients may be inputted in the device 100 by the staff members, for example via the user interface 208. Alternatively, the device 100 may receive data relating to the care need of the patients from the patient database 102. In the illustrated example, the care need 308 is given in terms of a number which indicates the amount of care the patient needs. The four patients 306a being associated with care unit 302a have care needs 9, 12, 8 and 11, the single patient 306b associated with care unit 302b has a care need of 20, and the two patients 306c associated with care unit 302c have care needs 38 and 42, respectively. Under the assumption that a higher care need is associated with a higher number, the patients 306a of care unit 302a have a mild care need, the patient 306b of care unit 302b has a moderate care need and the patients 306c of care unit 302c have a major care need. By considering the care needs 308 for the individual patients 306a-c, the device 100 may estimate the total care need 310a-c for each care unit 302a-c. The device 100 may for example accomplish this by first reading data relating to the care need 308 of the patients 306a-c from the patient database 102 and then estimating the care needs 308 for the individual patients 306a-c by using the processing unit 200. In the illustrated example the total care need 310a for care unit 302a is 40, the total care need 310b for care unit 302b is 20, and the total care need 310c for care unit 302c is 80. Consequently, each staff member of care unit 302a has to handle a care need of 10, each staff member of care unit 302b has to handle a care need of 20, and each staff member of care unit 302c has to handle a care need of 40. Thus, if the number of staff members is proportional to the number of patients, the staff resources are according to the example distributed between the care units in a non-efficient way. In the example, the patients 306c of care unit 302c are likely to not receive enough care while the staff resources of care unit 302a are likely to exceed the demand for care. The lower part of FIG. 3 is discussed below.

In order to avoid the above mentioned situation, a method for providing compensated staff data may be used. Such a method will now be described with reference to the flowchart of FIG. 4.

Figure 5:
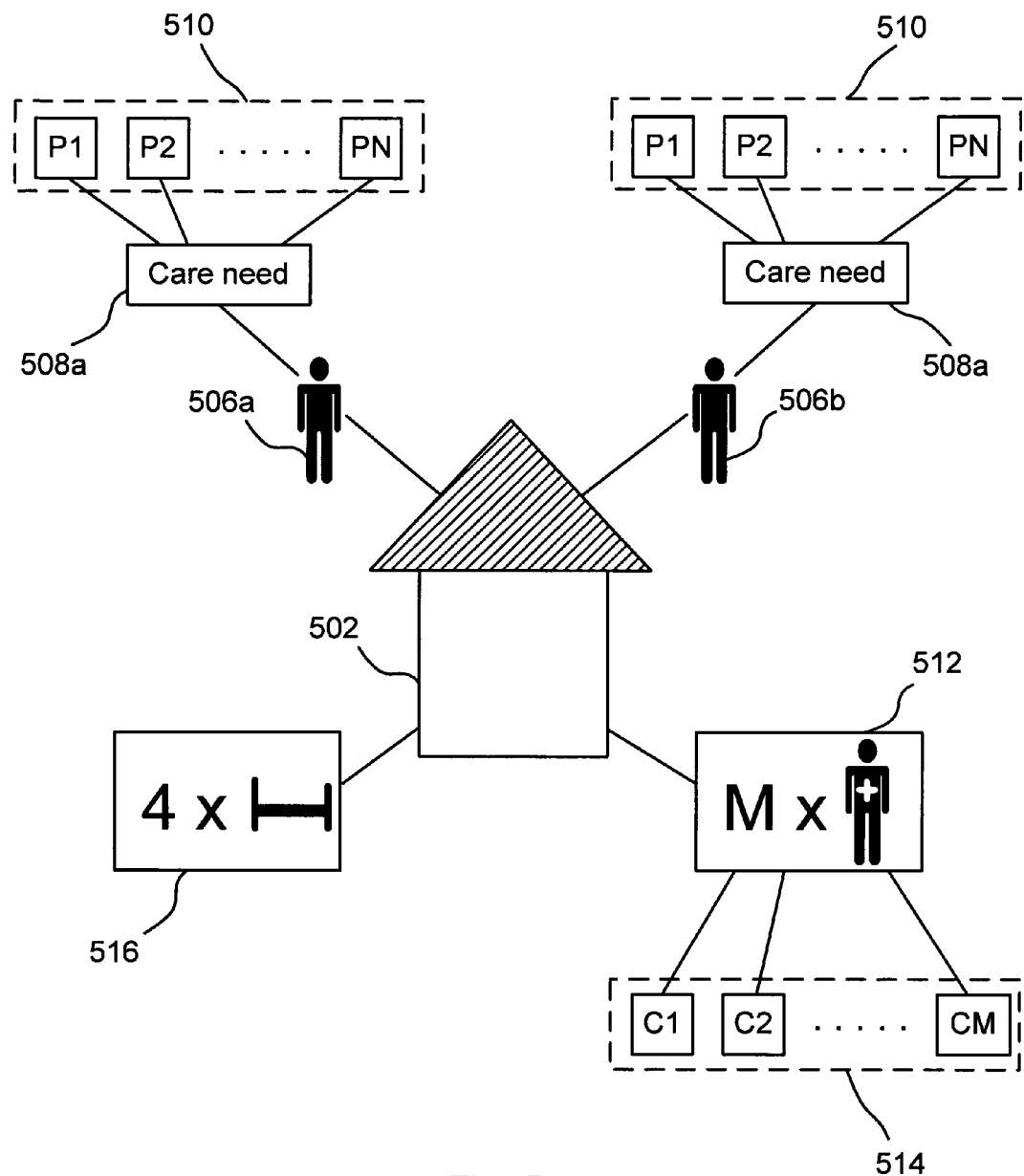
FIG. 5 is an illustration of a care unit observation according to embodiments.

In step 402 staff data comprising the number of staff members associated with each care unit observation is received. The staff data may for example be received by the receiver 202 of the device 100 from the staff database 104. The staff data may further comprise information relating to the competence of the staff members. FIG. 5 illustrates a care unit observation. The care unit observation is related to a care unit 502 which in turn is associated with staff data 512 indicating the number of staff members. In this case there are M staff members. Further, the staff members are associated with competences 514, here denoted by C1, . . . , CM. The competence 514 may relate to the experience of the staff member. For example, an experienced staff member may have worked with care for many years and may therefore perform the tasks faster than a non-experienced staff member. Alternatively, the competence 514 may relate to the qualifications of the staff member, such as if the staff member is a nurse or an assisting nurse. Since different care activities may require different qualifications of the staff members, this information may be taken into account by the device 100 when generating compensated staff data.

In step 404, patient data associated with a plurality of patients is received, each of the patients being associated with one care unit observation. The patient data, which may be received by the receiver 202 of the device 100, may for example be received from the patient database 102. In general, the patient data comprises information relating to a care need of a patient. More particularly, the patient data may be related to a number of care need parameters. In the illustration shown in FIG. 5, the care unit 502 is associated with two patients 506a-b. Each patient 506a, 506b has a care need 508a, 506b which in turn is associated with a plurality of care need parameters 510, here denoted by P1, . . . , PN. Thus, in this case the patient data comprises the care need parameters P1, . . . , PN for each patient.

The care need parameters 510 may reflect different kinds of needs of the patient 506a-b. Preferably, the number N of care need parameters is large enough to describe most of the patient's care need 508a-b. However, at the same time the number N of care need parameters 510 should be kept at a minimum in order to save computational effort and memory capacity of the device 100 and its related databases 102, 104, 106, 108. The inventors have found that by using the below care need parameters, an acceptable trade off between describing the care need at one hand and saving computational effort and memory capacity at the other hand may be achieved. Further, the inventors have found that the care need parameters may be chosen according to Table 1, wherein care need points for a particular patient have been identified by an "X". Still further, the care need parameters may be divided into three groups relating to general care, medical care, and cognitive care. By dividing the care need parameters into different groups the process of collecting the patient data may be simplified and made more efficient. Further, by dividing the care need parameters into groups the efficiency of the device 100 may be improved in some situations. One such situation is when the different groups correspond to different weighting factors. The processing unit 200 of device 100 may then determine the care need by adding the care need points for each group, dividing each group by the corresponding weight, and then adding the weighted sums for the three groups. This requires fewer operations than if each care need point is divided by a weight before computing a weighted sum. Hence, the efficiency of the device 100 may be improved by dividing the care need parameters into groups.

TABLE 1

Care need parameters and care need points

| Parameter | 0 | 1 | 2 | 3 | 4 |
|---|---|---|---|---|---|
| A. General care | | | | | |
| Nutrition | X | | | | |
| Washing upper body | | X | | | |
| Washing lower body | | | X | | |
| Toilet visits | | | | X | |
| Dressing/undressing | | X | | | |
| Shower/bath | | | | X | |
| Mobilization | | | X | | |
| Observation/supervision/alarm | | X | | | |
| Social activities | | X | | | |
| Total | 13 | 0 | 3 | 4 | 6 | 0 |
| B. Medical care | | | | | |
| Wound treatment | X | | | | |
| Catheter/stoma | X | | | | |
| Administration of drugs | | | X | | |
| Injection | | | X | | |
| Rehabilitation | | | | | X |
| Total | 7 | 0 | 1 | 2 | 0 | 4 |
| C. Cognitive Care | | | | | |
| Orientation/sense of locality | X | | | | |
| Verbal communication | | | X | | |
| Confusion | | X | | | |
| Anxiety | | | | X | |
| Temper | | | X | | |
| Total | 7 | 0 | 2 | 2 | 3 | 0 |

In step 406, a care need for each of the plurality of patients is determined based on the patient data received in step 402. The care need may for example be determined by the processing unit 200 of the device 100. More particularly, the device 100 may determine the care need for a patient in a number of steps. First the device 100 may read patient data relating to a plurality of care need parameters from the patient database 102. The patient data may then temporarily be stored in the memory 206 of the device 100. Next, the device 100 may by using the processor 200 determine the care need of the patient based on the patient data which is temporarily stored in the memory 206. Eventually, the device 100 may write the determined care need to the memory 206 or transmit it to the database 102. The care need is typically an estimate of the patient's total care need and it may be determined by the processing unit 200 by combining or weighting the care need parameters which are associated with the patient. For example, a staff member may classify a patient's care need for a particular care need parameter as being "mild", "moderate" or "major". The device 100 may then by using the processing unit 200 determine that the care need of a particular patient is "mild to moderate" if the patient has a mild care need for most care need parameters and a moderate care need for some care need parameters. Similarly, the device 100 may determine that the care need of a particular patient is "major to moderate" if a patient has a major care need for most care need parameters, a moderate care need for some care need parameters, and a mild care need for some care need parameters.

In order to make the process of determining a care need for a patient more efficient, and in particular to reduce the computational requirements on the processing unit 200 of the device 100, it may be advantageously if the care need relating to the individual care need parameters is given in terms of care need points. In Table 1 such care need points are illustrated by using numbers in a discrete scale, here from 0-4. For example, a care need point of 0 may indicate no care need and a care need point of 4 may indicate a major care need. In order to have a consistent scale of care need points between different patients, the interpretation of the care need points may for example be defined to the staff members who are classifying the patients in a manual. In Table 1 an example of care need parameters and corresponding care need points for a particular patient are shown. According to the table, the patient has no care need in terms of nutrition, here indicated by a cross in the box relating to a care need point of zero. Further, the patient need some help to wash his upper body, here indicated by a cross in the box relating to a care need point of one, etc. A staff member may input care need points for the patients in the patient database 102. For example a staff member may fill out an electronic form similar to Table 1 which then is written to the patient database 102.

The device 100 can be used to determine the care need for a patient from the care need points. For example, the device 100 may compute a weighted sum based on the care need points. In Table 1, the weights for the different care need parameters are set equal to unity, and thereby the individual care need points are added together in order to form the care need. In the illustrated example, the care need relating to general care is 13, the care need relating to medical care is 7 and the care need relating to cognitive care is 7. Hence, the care need for the patient becomes 27.

By computing a weighted sum care of need parameters, the device 100 may give different care need parameters different importance. For example, the processing unit 200 of the device 100 may weight care need parameters in accordance with the time duration for a staff member to perform the care. As an example, the time duration for giving an injection may be shorter than the time duration for showering a patient. Therefore, the processing unit 200 may assign a smaller weight for the care need parameter relating to injections than to the care need parameter relating to showering.

Alternatively, the care need points may be associated with a time duration. For example, each care need point may be associated with a number of minutes, such as three minutes. In this way, a patient who for instance needs help for nine minutes per day with toilets visits will be assigned a care need point of three for the care need parameter toilet visits. With this arrangement, the interpretation of a care need point is in terms of the time it takes a staff member to perform the care activity. In the example in Table 1, the patient thus needs 81 minutes (27×3 minutes) of care per day in case each care need point corresponds to three minutes of care. Moreover, by associating the care need points with a time duration, the care need points may be added without using a weight since the care need points are measured on the same time scale.

In step 408 care unit data comprising the number of beds associated with each of the plurality of care unit observations is received. The care unit data may for example be received by the receiver 202 of the device 100 from the care unit database 106. The number of beds is to be interpreted as the number of patients which the care unit may be able to take care of. Thus, the actual number of patients which currently is receiving care from the care unit may be smaller than the number of beds in the care unit. Often, however, the number of patients and the number of beds are equal. In the care unit observation illustrated in FIG. 5 the care unit 502 is associated with care unit data 516 indicating the number of beds, here illustrated by four beds.

In step 410 compensated staff data for one or more care units is generated based on the care need, the staff data and the care unit data. The compensated staff data may for example be determined by the processing unit 200 of the device 100. A method for generating compensated staff data will be described below with reference to FIG. 6.

In step 412 the compensated staff data generated in step 410 is transmitted. The compensated staff data may for example be transmitted by the transmitter 204 of the device 100 to a display.

The method may further comprise a step 414 of receiving care time data. The care time data may for example be received by the receiver 202 of the device 100 from the care time database 108. The care time data may associate each of the care need points with a time duration. For example, the care time data may associate each care need point with a number of minutes, such as three minutes. Alternatively, the care time data may associate each care need parameter with a time duration. The processing unit 200 of the device 100 may use such a time duration which is associated with a care need parameter as a weight when determining a care need by forming a weighted sum.

Figure 4:
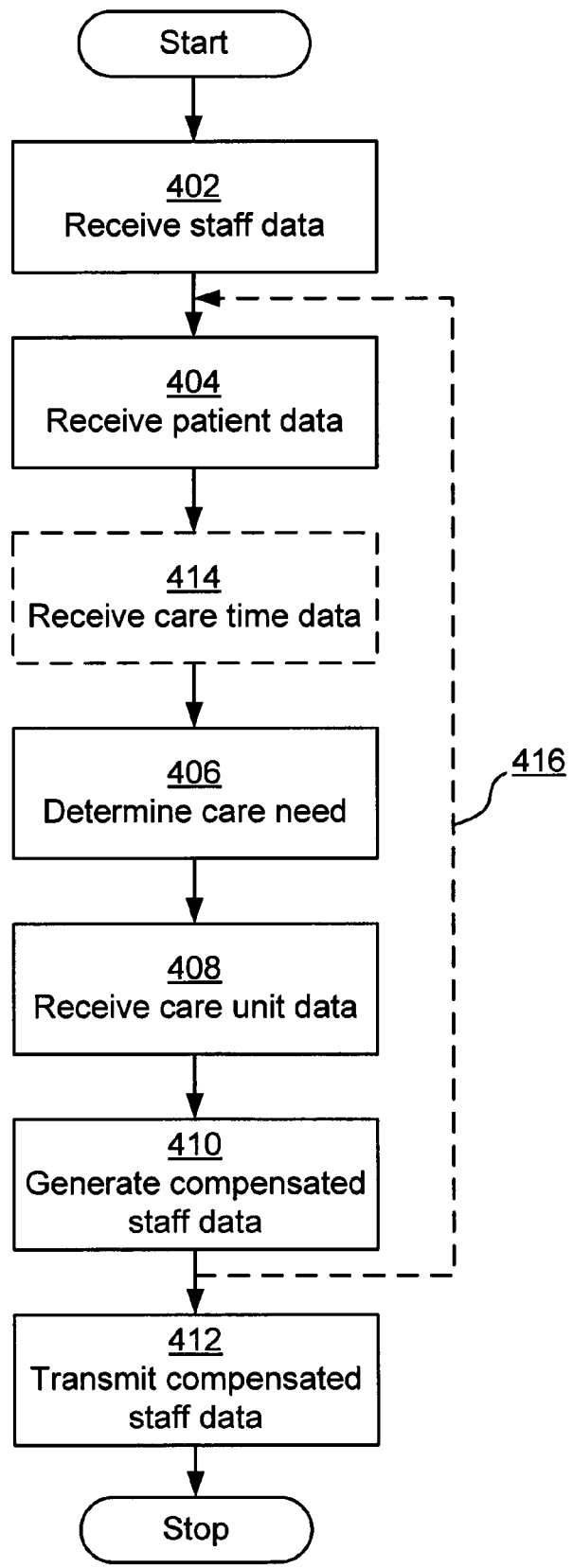
FIG. 4 is a flowchart of a method according to embodiments.

If a new set of care unit observations are made, it may be advantageous to update the compensated staff data. For example, the care need in the care units may have changed since the last care unit observations were made and therefore the compensated staff data previously provided by the method may not be current. Therefore, the method may further comprise updating the compensated staff data based on a new set of care unit observations. More precisely, the updating of compensated staff data may comprise receiving patient data for the new set of care unit observations, determining a care need for the new set of care unit observations, receiving care unit data for the new set of care unit observations, and generating updated compensated staff data based on the previously received data, the newly received data and the previously generated compensated staff data. In this way, the method may be applied in a recursive manner and the compensated staff data may be updated as the care need changes. In other words, a feedback 416 may be introduced in the method as illustrated in FIG. 4.

Figure 6:
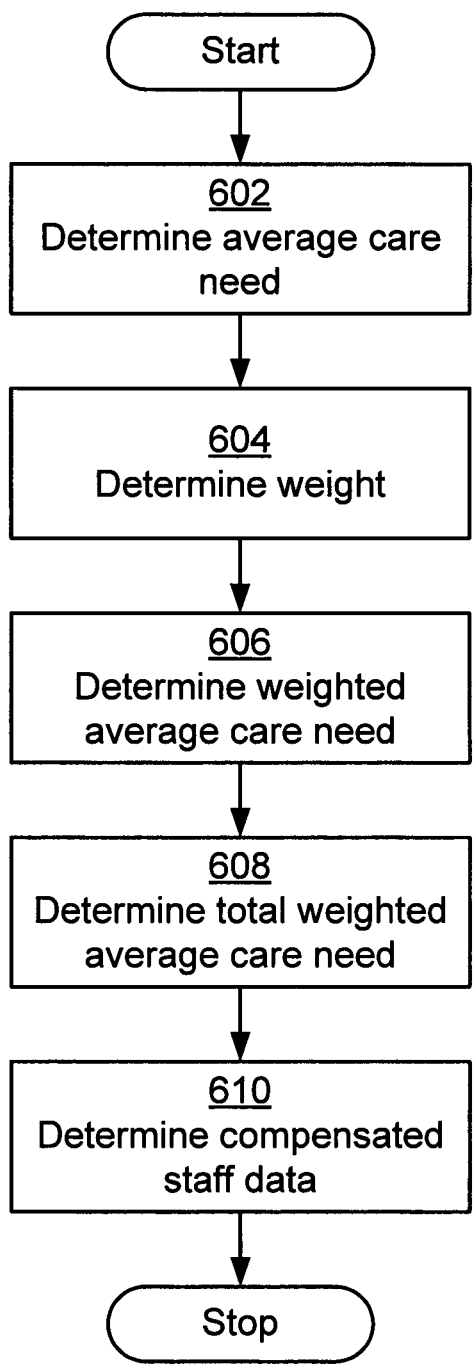
FIG. 6 is a flowchart of a method according to embodiments.

With reference to the flowchart in FIG. 6, a method for generating compensated staff data according to embodiments will now be described.

Figure 7:
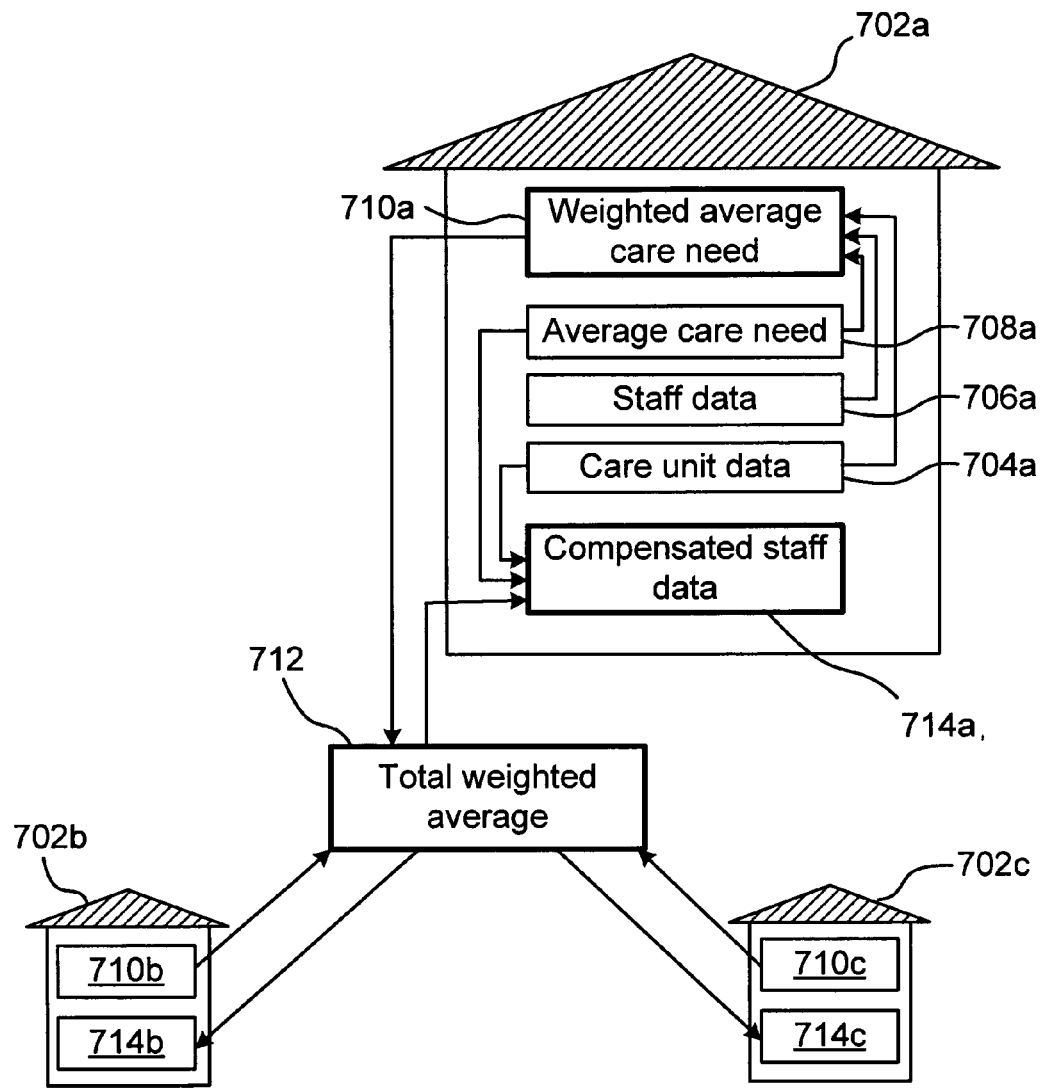
FIG. 7 is a schematic illustration of a method according to embodiments.

In step 602 the processing unit 200 of the device 100 may determine an average care need for each care unit observation based on the care need for each of the patients being associated to the care unit. In FIG. 7 three care unit observations 702*a-c* are illustrated. The care unit observations 702*a-c* correspond to care units 302*a-c* in FIG. 3. As disclosed above and shown in FIG. 3, the total care need for the three care units 302*a-c* are 40, 20 and 80, respectively. By dividing the total care need by the number of patients for each care unit, the average care needs for the illustrated care units become 10, 20 and 40 respectively, see also Table 2.

TABLE 2

Care unit observations, care need and associated compensated staff data.

| Care unit observation | Number of beds | Number of staff members | Average care need | Weighted average care need | Compensated number of staff members |
|---|---|---|---|---|---|
| 702a | 4 | 4 | 10 | 10 | 1.7 |
| 702b | 1 | 1 | 20 | 20 | 0.9 |
| 702c | 2 | 2 | 40 | 40 | 3.4 |
| Total: | 7 | 7 | | 23.3 | 6 |

In step 604, the processing unit 200 of the device 100 may determine a weight for each care unit observation. The weight may be based on the staff data and the care unit data. For example, the processing unit 200 may determine a weight by dividing the number of staff members for each care unit observation by the number of beds for the care unit observation. If such a weight is computed for the care unit observations 702*a-c* (corresponding to care units 302*a-c* in FIG. 3) the weight becomes equal to 1 for all care units observations.

In step 606, the processing unit 200 of the device 100 may determine a weighted average care need by weighting the average care need by using staff data and care unit data. Preferably, the weighted average care need is determined by using the weight determined in step 604. In FIG. 7 it is illustrated that care unit data 704*a*, staff data 706*a*, and average care need 708*a* may be combined into a weighted average care need 710*a* for care unit observation 702*a*. Likewise, weighted average care needs 710*b-c* may be determined for care unit observations 702*b-c*. If the weight determined in step 604 is used, the weighted average care needs 710*a-c* for care unit observations 702*a-c* become 10, 20 and 40 as shown in Table 2. The interpretation of the weighted average care need 710*a-c* is the amount of care need that one staff member handles on average in the different care unit observations 702*a-c*. From Table 2 it follows that the workload for the staff members in care unit observation 702*c* is twice the workload for the staff members in care unit observation 702*b* and four times the workload for the staff members in care unit observation 702*a*.

In step 608, the processing unit 200 of the device 100 may compute a total weighted average by averaging the weighted average care need for the plurality of care unit observations. In FIG. 7 it is illustrated that the weighted average care needs 710*a-c* are combined into a total weighted average care need 712. As the weighted average care need 710*a-c* has the interpretation of being the care need that one staff member handles on average in the different care units, the total weighted average 712 has the interpretation of being the care need that one staff member may handle on average regardless of which care unit observation 702*a-c* the staff member belongs to. Thus, by combining the weighted average care need 710*a-c* for all care unit observations, the device 100 may provide a good estimate of the amount of care need that each staff member may handle. In the example in Table 2 the total weighted average is equal to 70/3=23.3.

Eventually, in step 610, the processing unit 200 of the device 100 may determine compensated staff data by using the total weighted average. The compensated staff data may be determined for each care unit observation by combining the total weighted average with the average care need and the care unit data. In FIG. 7 it is illustrated that the total weighted average 712 may be combined with the average care need 708a and the care unit data 704a in order to determine compensated staff data 714a for care unit observation 702a. Similarly, compensated staff data 714b-c may be determined for the other care unit observations 702b-c. For example, the processing unit 200 of the device 100 may determine compensated staff data by multiplying the average care need 708a with the number of beds and by dividing it by the total weighted average 712. In this way, the compensated staff data 714a-c is determined by dividing the total care need for each care unit observation by the care need handled on average by each staff member. In the example of Table 2, compensated staff data has been determined for the three care unit observations. The compensated number of staff members is 1.7, 0.9 and 3.4, respectively, for care unit observations 702a-c. This is also illustrated in the lower part of FIG. 3 where compensated staff data 304a'-c' are shown for the care units 302a-c. Note that the total number of staff members in the staff data 304a-c is seven while the total number of staff members in the compensated staff data 304a'-c' is six. Thus, by applying the method the resources may not only be redistributed but they also be increased or decrease depending on the care unit observations.

Further, the device 100 may take the competence of the staff members into account when generating compensated staff data. For example, if the staff members are divided into groups based on their qualifications, the method may be applied one time per staff group. Moreover, the care need parameters may be chosen based on the qualifications of the staff. Alternatively, if the competence of the staff members is given in terms of their working experience, the compensated staff data may be adjusted for this fact as well. For example, a very experienced staff member may correspond to two standard staff members, where a standard staff member is a staff member having average experience. Thus, if the number of staff members in the compensated staff data equals two, these two staff members may be replaced by one experienced staff member.

In general the care unit observations may correspond to any number of care units. For example, the care unit observations may correspond to different care units or several care unit observations may correspond to the same care unit. The care unit observations 702a-c may thus correspond to observations of different care units or three observations of the same care unit. Alternatively, two of the care unit observations, such as care unit observations 702a-b, may correspond to the same care unit and care unit observation 702c may correspond to a different care unit.

Figure 8:
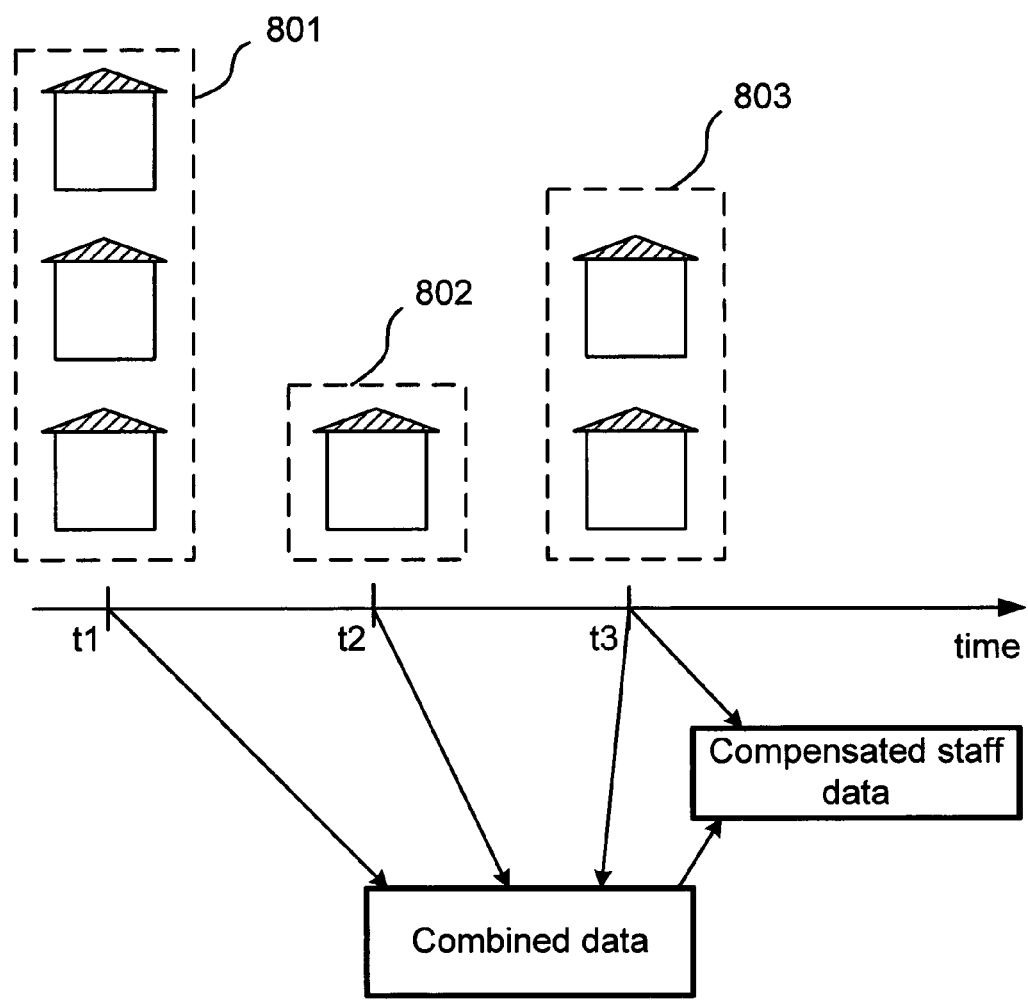
FIG. 8 is a schematic illustration of a method according to embodiments.

Further, the care unit observations may be associated with different points in time. This is illustrated in FIG. 8 which shows a time line. At a first time point t1 a first group 801 comprising three care unit observations is observed. At a later time point t2 a second group 802 of care unit observations comprising two care unit observations is observed and at a still later time point t3 a third group 803 comprising two care unit observations is observed. The data associated with the care unit observations from all three groups 801-803 may be combined in order to generate compensated staff data as previously described. In the example, the compensated staff data is only generated for the care units which are associated to the care unit observations comprised in the third group 803 of care unit observations.

The person skilled in the art realizes that the present invention by no means is limited to the exemplary embodiments described above. On the contrary, many modifications and variations are possible within the scope of the appended claims. For example, the generating of the compensated staff data may be performed in different ways. One such way may be to first compute an average care need per staff member by summing the care needs for all patients in all care unit observations and divide it by the total number of staff members in all care unit observations, and then generate compensated staff data by dividing the total care need in each care unit observation with the average care need per staff member. In the example in FIG. 3, the compensated staff data generated in this way results in 2 staff members for care unit 302a, one staff member for care unit 302b, and 4 staff members for care unit 303c. Note that with this method the total number of staff members is kept constant and the staff members are only among the care units.

The invention claimed is:

1. Method performed in a device for providing compensated staff data by redistributing staff resources between a plurality of care units, said method comprising:

receiving staff data comprising the number of staff members associated with each care unit, receiving patient data associated with a plurality of patients, wherein each of said plurality of patients is associated with one of said plurality of care units, said patient data relating to a plurality of care need parameters, determining, by a processing unit, a care need for each of said plurality of patients based on said patient data, receiving care unit data comprising the number of beds associated with each of said plurality of care units, generating, by the processing unit, compensated staff data for each of said plurality of care units by combining said care need, said staff data and said care unit data associated with all of the plurality of care units, by for each care unit, determining an amount of care need to be handled per staff member in the care unit as a weighted average care need formed by dividing an average of the care need of the patients associated with the care unit with a weight obtained by dividing the number of staff members of the care unit with the number of beds of the care unit, determining an average amount of care need to be handled per staff member in the plurality of care units as a total weighted average obtained by averaging the weighted average care need of the plurality of care units, for each care unit, multiplying the average care need of the patients associated with the care unit by the number of beds of the care unit and dividing it by the total weighted average in order to obtain the compensated staff data of the care unit, and transmitting said compensated staff data.

2. The method according to claim 1, wherein said patient data associates each patient with a plurality of care need points, wherein each of said plurality of care need points corresponds to one of said plurality of care need parameters, and wherein said determining a care need for each of said plurality of patients comprises adding, for each patient, said plurality of care need points.

3. The method according to claim 2, wherein each of said plurality of care need points is associated with a time duration.

4. The method according to claim 3, further comprising receiving care time data which associates each of said plurality of care need points with said time duration.

5. The method according to claim 2, wherein each of said plurality of care need points takes values in a discrete set of ordered numbers.

6. The method according to claim 1, wherein said staff data further comprises information relating to a competence of said number of staff members, wherein said competence of said number of staff members is used in said step of generating compensated staff data.

7. The method according to claim 1, wherein said plurality of care need parameters are grouped into three groups relating to general care, medical care and cognitive care, wherein the group relating to general care comprises the care need parameters nutrition, washing upper body, washing lower body, toilet visits, dressing/undressing, mobilization, observation/supervision/alarm and social activities, the group relating to medical care comprises the care need parameters wound treatment, catheter/stoma, administration, injection, rehabilitation, and the group relating to cognitive care comprises the care need parameters orientations/sense of locality, verbal communication, confusion, anxiety, and temper.

8. Device for providing compensated staff data by redistributing staff resources between a plurality of care units, said device comprising:
a receiver arranged to receive staff data comprising the number of staff members associated with each care unit, to receive patient data associated with a plurality of patients, wherein each of said plurality of patients is associated with one of said plurality of care units, said patient data relating to a plurality of care need parameters, and to receive care unit data comprising the number of beds associated with each of said plurality of care units,
a processing unit arranged to determine a care need for each of said plurality of patients based on said patient data, and to generate compensated staff data for each of said one or more care units by combining said care need, said staff data and said care unit data associated with all of the plurality of care units, by
for each care unit, determining an amount of care need to be handled per staff member in the care unit as a weighted average care need formed by dividing an average of the care need of the patients associated with the care unit with a weight obtained by dividing the number of staff members of the care unit with the number of beds of the care unit,
determining an average amount of care need to be handled per staff member in the plurality of care units as a total weighted average obtained by averaging the weighted average care need of the plurality of care units,
for each care unit, multiplying the average care need of the patients associated with the care unit by the number of beds of the care unit and dividing it by the total weighted average in order to obtain the compensated staff data of the care unit,
and
a transmitter arranged to transmit said compensated staff data.

9. A non-transitory computer-readable medium comprising computer program code portions adapted, when loaded and executed on a computer, to perform a method for providing compensated staff data by redistributing staff resources between a plurality of care units, the method comprising:
receiving staff data comprising the number of staff members associated with each care unit,
receiving patient data associated with a plurality of patients, wherein each of said plurality of patients is associated with one of said plurality of care units said patient data relating to a plurality of care need parameters,
determining, by a processing unit, a care need for each of said plurality of patients based on said patient data,
receiving care unit data comprising the number of beds associated with each of said plurality of care units,
generating, by the processing unit, compensated staff data for each of said plurality of care units by combining said care need, said staff data and said care unit data associated with all of the plurality of care units, by
for each care unit, determining an amount of care need to be handled per staff member in the care unit as a weighted average care need formed by dividing an average of the care need of the patients associated with the care unit with a weight obtained by dividing the number of staff members of the care unit with the number of beds of the care unit,
determining an average amount of care need to be handled per staff member in the plurality of care units as a total weighted average obtained by averaging the weighted average care need of the plurality of care units,
for each care unit, multiplying the average care need of the patients associated with the care unit by the number of beds of the care unit and dividing it by the total weighted average in order to obtain the compensated staff data of the care unit,
and
transmitting said compensated staff data.

* * * * *